(12) United States Patent
Bolea (10) Patent No.: US 8,840,840 B2
(45) Date of Patent: Sep. 23, 2014

(54) ILLUMINATION APPARATUS AND METHODS FOR A BIOLOGICAL GROWTH PLATE SCANNER

(75) Inventor: Phillip A. Bolea, Grant, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 13/513,900

(22) PCT Filed: Dec. 2, 2010

(86) PCT No.: PCT/US2010/058646
§ 371 (c)(1),
(2), (4) Date: Jun. 5, 2012

(87) PCT Pub. No.: WO2011/071734
PCT Pub. Date: Jun. 16, 2011

(65) Prior Publication Data
US 2012/0244574 A1  Sep. 27, 2012

Related U.S. Application Data

(60) Provisional application No. 61/267,671, filed on Dec. 8, 2009.

(51) Int. Cl.
| | | |
|---|---|---|
| *G01N 21/00* | (2006.01) | |
| *C12Q 1/04* | (2006.01) | |
| *C12M 1/00* | (2006.01) | |
| *C12M 1/34* | (2006.01) | |
| *C12M 3/00* | (2006.01) | |
| *G01N 21/25* | (2006.01) | |

(52) U.S. Cl.
CPC ...... *G01N 21/255* (2013.01); *G01N 2201/0636* (2013.01); *G01N 2201/0634* (2013.01); *G01N 2201/0632* (2013.01)
USPC ..... 422/82.05; 435/34; 435/283.1; 435/288.7

(58) Field of Classification Search
None
See application file for complete search history.

(56) References Cited

U.S. PATENT DOCUMENTS

| | | | |
|---|---|---|---|
| 5,403,722 A | | 4/1995 | Floeder et al. |
| 5,453,849 A | * | 9/1995 | Copenhaver et al. ......... 358/475 |
| 5,573,950 A | | 11/1996 | Graessle et al. |
| 5,997,155 A | | 12/1999 | Ducharme et al. |
| 7,298,886 B2 | | 11/2007 | Plumb et al. |
| 7,496,225 B2 | | 2/2009 | Graessle et al. |
| 8,094,916 B2 | | 1/2012 | Graessle et al. |
| 2004/0101954 A1 | | 5/2004 | Graessle et al. |
| 2004/0102903 A1 | * | 5/2004 | Graessle et al. ................ 702/19 |
| 2004/0125344 A1 | * | 7/2004 | Matsui ............................ 353/94 |
| 2005/0053265 A1 | | 3/2005 | Graessle et al. |
| 2005/0053266 A1 | | 3/2005 | Plumb et al. |

FOREIGN PATENT DOCUMENTS

| | | |
|---|---|---|
| EP | 1 074 610 | 2/2001 |
| JP | 2006-508362 | 3/2006 |
| JP | 2008-102389 | 5/2008 |
| WO | WO 2004/051283 | 6/2004 |

* cited by examiner

*Primary Examiner* — Jill Warden
*Assistant Examiner* — Julie Tavares (57) ABSTRACT

Illumination apparatus for illuminating growth plates in a biological growth plate (122) scanner are described herein, the apparatus including one or more illumination modules (140) for illuminating the front surface of the biological growth plate located (122) on a plate support surface (120) in the scanner. The illumination modules may include a plurality of light emitters (142), a homogenization cavity (141), an extraction element and a concentration element to (144), e.g., improve uniformity in the illumination delivered to the biological growth plate (122).

25 Claims, 3 Drawing Sheets

ILLUMINATION APPARATUS AND METHODS FOR A BIOLOGICAL GROWTH PLATE SCANNER

CROSS REFERENCE TO RELATED APPLICATIONS

This application claims the benefit of U.S. Provisional Patent Application No. 61/267,671, filed Dec. 8, 2009, which is incorporated herein by reference in its entirety.

Biological safety is a paramount concern in modern society. Testing for biological contamination in foods or other materials has become an important and sometimes mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

In particular, a wide variety of biological growth media have been developed. As one example, biological growth media in the form of growth plates have been developed by 3M Company (hereafter "3M") of St. Paul, Minn. Biological growth plates are sold by 3M under the trade name PETRI-FILM plates. Biological growth plates can be utilized to facilitate the rapid growth and detection and enumeration of bacteria or other biological agents commonly associated with food contamination, including, for example, aerobic bacteria, *E. coli*, coliform, enterobacteriaceae, yeast, mold, *Staphylococcus aureus, Listeria, Campylobacter*, and the like. The use of PETRIFILM plates, or other growth media, can simplify bacterial testing of food samples.

Biological growth media can be used to identify the presence of bacteria so that corrective measures can be performed (in the case of food testing) or proper diagnosis can be made (in the case of medical use). In other applications, biological growth media may be used to rapidly grow bacteria or other biological agents in laboratory samples, e.g., for experimental purposes.

Biological growth plate scanners refer to devices used to read or count bacterial colonies, or the amount of a particular biological agent on a biological growth plate. For example, a food sample or laboratory sample can be placed on a biological growth plate, and then the plate can be inserted into an incubation chamber. After incubation, the biological growth plate can be placed into the biological growth plate scanner for automated detection and enumeration of bacterial growth. Examples of some biological growth plate scanners may be found in US Patent Application Publication Nos. 2004/0101954 and 2004/0102903 and U.S. Pat. No. 7,496,225 (all to Graessle et al.).

SUMMARY

Illumination apparatus for illuminating growth plates in a biological growth plate scanner are described herein, the apparatus including one or more illumination modules for illuminating the front surface of the biological growth plate located on a plate support surface in the scanner. The illumination modules may include a plurality of light emitters, a homogenization cavity, an extraction element and a concentration element to, e.g., improve uniformity in the illumination delivered to the biological growth plate.

In one aspect, one or more embodiments of an illumination apparatus for illuminating biological growth plates in a biological growth plate scanner as described herein include a plate support surface comprising a first side and a second side located opposite from the first side and a first illumination module oriented to illuminate a first portion of the plate support surface. The first illumination module comprises a homogenization cavity comprising an interior surface, wherein the interior surface is diffusely reflective, wherein the interior surface of the homogenization cavity comprises a tube that comprises a longitudinal axis extending along a length of the homogenization cavity, and wherein the longitudinal axis is aligned with the first side of the plate support surface; an illumination source operably connected to the homogenization cavity, wherein the illumination source emits light into the homogenization cavity; an extraction element in the homogenization cavity through which the light emitted into the homogenization cavity exits from the homogenization cavity, wherein the extraction element comprises a length aligned with the longitudinal axis, and wherein the illumination source, the interior surface of the homogenization cavity, and the extraction element are arranged such that the light emitted into the homogenization cavity by the illumination source reflects from the interior surface of the homogenization cavity at least once before exiting the homogenization cavity through the extraction element; and a concentration element operably connected to the homogenization cavity and arranged such that the light exiting the homogenization cavity through the extraction element must pass through the concentration element; wherein the light passing through the concentration element from the extraction element exits from the concentration element within a selected angular range $\alpha$ (alpha) of 60 degrees or less.

In some embodiments, the apparatus may include a second illumination module oriented to illuminate a second portion of the plate support surface. The second illumination module comprises a homogenization cavity comprising an interior surface, wherein the interior surface is diffusely reflective, wherein the interior surface of the homogenization cavity comprises a tube that comprises a longitudinal axis extending along a length of the homogenization cavity, and wherein the longitudinal axis is aligned with the second side of the plate support surface; an illumination source operably connected to the homogenization cavity, wherein the illumination source emits light into the homogenization cavity; an extraction element in the homogenization cavity through which the light emitted into the homogenization cavity exits from the homogenization cavity, wherein the extraction element comprises a length aligned with the longitudinal axis, and wherein the illumination source, the interior surface of the homogenization cavity, and the extraction element are arranged such that the light emitted into the homogenization cavity by the illumination source reflects from the interior surface of the homogenization cavity at least once before exiting the homogenization cavity through the extraction element; and a concentration element operably connected to the homogenization cavity and arranged such that the light exiting the homogenization cavity through the extraction element must pass through the concentration element; wherein the light passing through the concentration element from the extraction element exits from the concentration element within a selected angular range $\alpha$ (alpha) of 60 degrees or less.

In some embodiments, the first portion and/or the second portion of the plate support surface illuminated by the first and/or second illumination modules comprises substantially all of the plate support surface.

In some embodiments, the plate support surface defines an imaging plane, and the concentration element of the first and/or second illumination modules comprises a central emission axis within a center of the angular range α (alpha), and further wherein the central emission axis forms an incidence angle β (beta) with an axis normal to the imaging plane that is 75 degrees or less. In some embodiments, the incidence angle β (beta) is 50 degrees or more. In some embodiments, the selected angular range α (alpha) of the concentration element is 45 degrees or less. In some embodiments, the incidence angle β (beta) and the selected angular range α (alpha) of the first and/or second illumination modules are selected such that the plate support surface is illuminated with an illumination intensity that varies by ±10% or less over the plate support surface.

In some embodiments, the tube of the homogenization cavity of the first and/or second illumination modules comprises a circular cylindrical tube.

In some embodiments, the plate support surface defines an imaging plane, and the concentration element of the first and/or second illumination modules comprises a central emission axis within a center of the angular range α (alpha), wherein the central emission axis forms an incidence angle β (beta) with an axis normal to the imaging plane, and further wherein the first and/or second illumination modules rotate relative to the longitudinal axis of the homogenization cavity to adjust the incidence angle β (beta) of the rotated illumination module. In some embodiments, the first and/or second illumination modules rotate about the longitudinal axis of their respective homogenization cavity.

In some embodiments, the concentration element of the first and/or second illumination modules comprises a pair of parabolic surfaces. In some embodiments, the parabolic surfaces comprise diffusely reflective surfaces.

In another aspect, a method of illuminating a plate support surface of biological growth plate scanner is described herein, the method comprising: positioning a growth plate on the plate support surface of an illumination apparatus as described herein; and illuminating the growth plate using the first and second illumination modules.'

Some embodiments of the methods described herein may include rotating the first and/or second illumination modules relative to the longitudinal axis of the homogenization cavity of the first and/or second illumination module; measuring the illumination intensity across the plate support surface after and/or while rotating the illumination module. The rotating may involve rotating the first illumination module about the longitudinal axis of the homogenization cavity of the first illumination module.

In another aspect, a biological growth plate scanner is described herein that includes an imaging device; an image processor operably connected to the imaging device; and an illumination apparatus as described herein.

The above summary is not intended to describe each embodiment or every implementation of the apparatus and methods described herein. Rather, a more complete understanding of the apparatus and methods will become apparent and appreciated by reference to the following Description of Illustrative Embodiments and claims in view of the accompanying figures of the drawing.

DESCRIPTION OF ILLUSTRATIVE EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of this disclosure.

Exemplary embodiments shall generally be described with reference to FIGS. 1-3. Elements from one embodiment may be used in combination with elements of the other embodiments, and that the possible embodiments of such apparatus using combinations of features set forth herein is not limited to the specific embodiments shown in the figures and/or described herein. Further, the embodiments described herein will include many elements that are not necessarily shown to scale. Further, the size and shape of various elements herein may be modified without departing from the scope of the present disclosure, although one or more shapes and sizes, or types of elements, may be advantageous over others.

As used herein, "a," "an," "the," "at least one," and "one or more" are used interchangeably. The term "and/or" (if used) means one or all of the listed elements or a combination of any two or more of the listed elements.

Further, as used herein, the term "light" may be defined as any electromagnetic energy that is suitable for imaging by the imaging devices described herein. In some embodiments, light may be limited to electromagnetic energy within the spectrum visible to the naked human eye, but may also include or alternatively be limited to, e.g., ultraviolet energy, infrared energy, etc.

The illumination apparatus can be used to illuminate the front surface of biological growth plates for biological growth plate scanners that obtain images of biological growth plates. The images can then be analyzed to detect biological growth on the growth plates. For example, the scanner may count or otherwise quantify an amount of biological agents that appear in the image, such as a number of bacteria colonies. In this manner, the illumination apparatus described herein can be used in biological growth plate scanners to potentially automate the analysis of biological growth plates. Examples of some biological growth plate scanners with which the illumination apparatus described herein can be used may include, but are not limited to those described in U.S. Patent Application Publication Nos. 2004/0101954 and 2004/0102903; and U.S. Pat. No. 7,496,225 (all to Graessle et al.).

As described herein, the illumination apparatus may include one or more illumination modules to illuminate a biological growth plate located on the plate support surfaces of the biological growth plate scanners. The illumination modules may be in the form of a multi-color illumination module that illuminates the biological growth plate with different illumination colors. In such a system, a monochromatic image capture device can be used to capture images of the biological growth plate during illumination of the growth plate with each of the illumination colors. A processor can be used to combine the images to form a composite multi-color image, and analyzes the composite image and/or individual components of the composite image to produce an analytical result such as a colony count or presence/absence result. Although different illumination colors may be used to obtain images that may or may not be combined, in other embodiments, the illumination modules may use monochromatic and/or wide-spectrum illumination to obtain one or more images that may or may not be combined.

Biological growth plate scanners may optionally include back illumination components in addition to the illumination apparatus described herein. The back illumination component may, in some embodiments, deliver diffused illumination to the back surface of a biological growth plate (i.e., the surface of the biological growth plate that faces the plate support surface). Examples and further discussion of back illumination of biological growth plates may be found in, e.g., U.S. Patent Application Publication No. US 2004/0101954 (Graessle et al.) entitled BACK SIDE PLATE ILLUMINATION FOR BIOLOGICAL GROWTH PLATE SCANNER.

The scanners and the illumination apparatus described herein may be useful with a variety of biological growth plates. For example, the invention may be useful with different plate-like devices for growing biological agents to enable detection and/or enumeration of the agents, such as thin-film culture plate devices, Petri dish culture plate devices, and the like. As a result, the term "biological growth plate" will be used broadly herein to refer to a medium suitable for growth of biological agents to permit detection and enumeration of the agents by a scanner. In some embodiments, the biological growth plate can be housed in a cassette that supports multiple plates, e.g., as described in U.S. Pat. No. 5,573,950 to Graessle et al.

Figure 1:
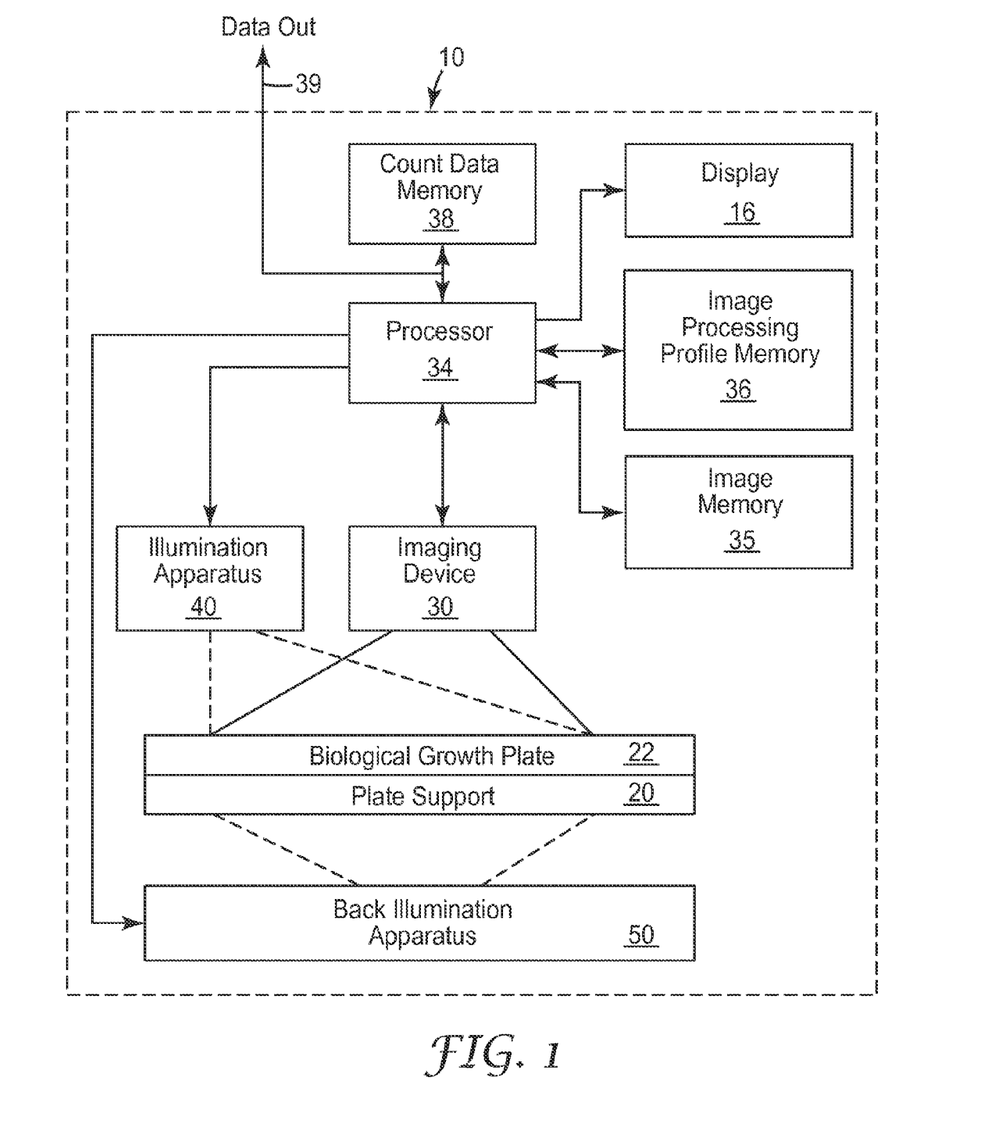
FIG. 1 is a block diagram illustrating potential components of one embodiment of an illumination apparatus for a biological growth plate scanner.

FIG. 1 is a block diagram illustrating various components in one embodiment of a biological growth plate scanner 10 including an illumination apparatus as described herein. A biological growth plate 22 is positioned within biological growth plate scanner 10 on a plate support 20. The plate support 20 preferably places biological growth plate 22 in position to be imaged by an imaging device 30 (e.g., at a desired focal plane of imaging device 30). The biological growth plate 22 may be placed in position on a tray, cassette, drawer, etc. as discussed in, e.g., U.S. Patent Application Publication No. US 2004/0102903 to Graessle et al., using an automated intake system as described in, e.g., U.S. Pat. No. 7,496,225 to Graessle et al., or any other suitable form of positioning the biological growth plate 22 for illumination and imaging.

In some embodiments, the imaging device 30 may be in the form of a line or area scanner that is positioned to capture an image of the surface of growth plate 22 when it is on the plate support 20. In other embodiments, the imaging device 30 may take other forms, e.g., a camera, etc. If provided in the form of a camera, the imaging device may potentially be in the form of a two-dimensional, monochromatic camera.

The scanner 10 include an illumination apparatus 40 that may include one or more illumination modules positioned to illuminate the front surface of the growth plate 22 (where the front surface is the surface facing away from the plate support 20 and facing towards the imaging device 30).

The scanner 10 may also include an optional back illumination apparatus 50 that can be used to provide illumination to the back surface of a growth plate 22 on the plate support 20 (where the back surface is the surface of the growth plate 22 facing the plate support 20).

In general, imaging device 30 captures images of biological growth plate 22, or at least a growth region within the biological growth plate 22, during illumination of the biological growth plate by the illumination apparatus 40 and/or the back illumination apparatus 50. In some embodiments, illumination duration, intensity, wavelength (e.g., color), may be selected and controlled according to requirements of different biological growth plates.

In the depicted embodiment, a processor 34 controls the operation of imaging device 30. In operation, processor 34 may also be used to control the one or more illumination apparatuses 40 and/or the back illumination apparatus 50 to illuminate biological growth plate 22 in order to capture images of biological growth plate 22. The images may, in some embodiments, be stored in image memory 35.

Processor 34 preferably analyzes the image or images of biological growth plate 22 to produce an analytical result, such as a colony count or a presence/absence result. If sequential multi-color imaging is performed (as described in, e.g., U.S. Patent Application Publication No. US 2004/0102903 to Graessle et al.), processor 34 can receive image data representing the scanned images from imaging device 30 during illumination with each of the different illumination colors, and combine the images to form a multi-color composite image. Processor 34 may take the form of, e.g., a microprocessor, digital signal processor, application specific integrated circuit (ASIC), field programmable gate array (FPGA) or other integrated or discrete logic circuitry programmed or otherwise configured to provide functionality as described herein.

In some embodiments, processor 34 may extract or segregate a portion of the image to isolate a plate type indicator as described in, e.g., U.S. Patent Application Publication No. US 2004/0102903 to Graessle et al. Using machine vision techniques, for example, processor 34 may analyze plate type indicator to identify a plate type associated with biological growth plate 22. Processor 34 then retrieves an image processing profile from image processing profile memory 36. The image processing profile corresponds to the detected plate type, and may specify image capture conditions and image analysis conditions.

As described herein, processor 34 processes the image or images and produces an analytical result, such as a colony count or a presence/absence result, which can be presented to a user via display 16. Processor 34 also may store the analytical result in memory, such as count data memory 38, for later retrieval from scanner 10. The data stored in count data memory 38 may be retrieved, for example, by a host computer that communicates with biological growth plate scanner 10 via a communication port 39, e.g., a universal serial bus (USB) port, IEEE 1494 port, etc. The host computer may compile analytical results for a series of biological growth plates 22 presented to biological growth plate scanner 10 for analysis.

Figure 2:
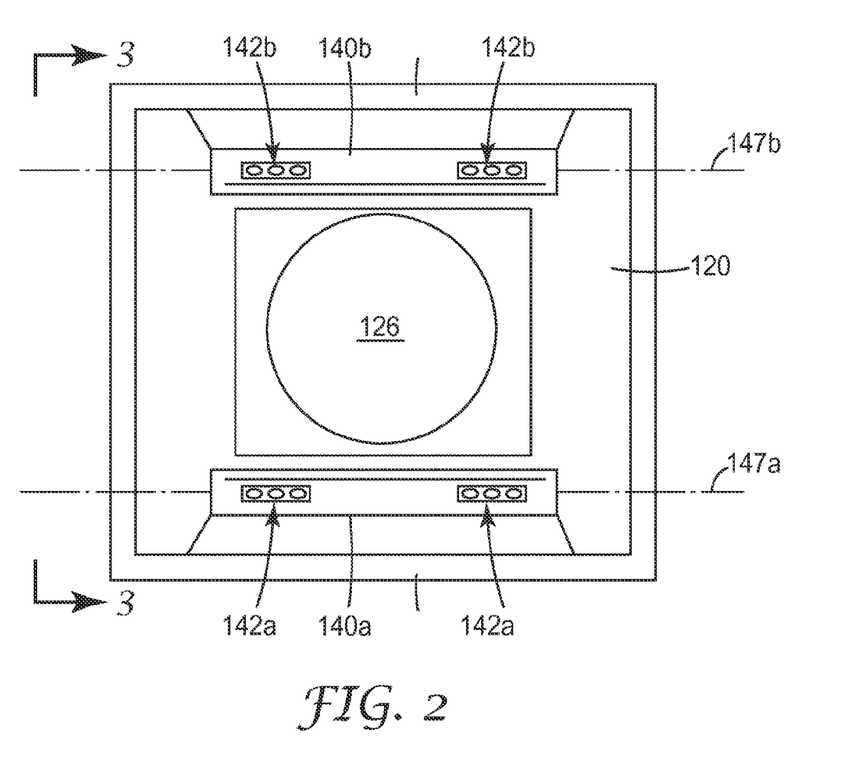
FIG. 2 is a plan view illustrating a biological growth plate on a plate support surface and a pair of illumination modules used to illuminate the front surface of a biological growth plate on the plate in one embodiment of a biological growth plate scanner as described herein.

FIG. 2 is a plan view of one embodiment of a plate support 120 with a biological growth plate 122 positioned thereon. The growth plate 122 may, in some embodiments, include a defined growth region 126 located on the larger growth plate 122. Also depicted in FIG. 2 are two illumination modules 140a and 140b that are provided as a part of an illumination apparatus to illuminate the growth plate 122. Although two illumination modules are depicted in this embodiment, some embodiments of the illumination apparatus described herein may include only one illumination module, while other embodiments may include three, four, or more illumination modules.

In the embodiment of FIG. 2, the illumination modules 140a and 140b are positioned on opposing sides of the plate support 120 (and, thus, preferably on opposing sides of a growth plate 122 positioned on the plate support 120). In other embodiments, however, illumination modules may be provided in other positions, e.g., on two adjacent sides, etc. In some embodiments, each of the illumination modules 140a and 140b may be described as having a longitudinal axis 147a/147b extending along a side of the plate support 120.

The illumination modules 140a and 140b may be described as illuminating an imaging area on the plate support 120, where the imaging area may correspond generally to the area occupied by a growth plate 122. Where multiple illumination modules are used, it may be beneficial if each illumination module is selected and arranged such that it illuminates a selected portion of the imaging area. In some embodiments, that selected portion may be all of the imaging area (which, as discussed herein, may include all of the growth plate 122) or the selected portion may be only a fraction of the imaging area. For example, if two illumination modules are used, the illumination modules 140a and 140b may each illuminate half of the imaging area.

Each illumination module 140a and 140b may include one or more illumination sources 142a and 142b. In the depicted embodiment, each of the illumination modules 140a and 140b includes two illumination sources 142a and 142b spaced apart along a longitudinal axis extending along a length of the illumination module, although the illumination modules 140a and 140b may include more than two illumination sources 142a and 142b in some embodiments. Although the depicted illumination modules include the same number of illumination sources, different illumination modules may contain different numbers of illumination sources.

Illumination sources 142a and 142b may be provided in a variety of different forms. In some embodiments, the illumination sources 142a and 142b may include only one illumination element or an array of multiple illumination elements that can be activated individually and/or in combination to provide illumination of a growth plate. Each of the illumination elements may be the same or different. For example, in some embodiments, each illumination source 142a and 142b may include LED illumination elements that provide red, green, and a blue light. The LED illumination elements may preferably be separately activated to illuminate biological growth plate 122 with a selected color of light. Upon activation of the individual LED illumination elements, light from the illumination module provides front illumination to biological growth plate 122. An imaging device can then be used to capture one or more images of biological growth plate 122 during, e.g., successive exposure cycles.

Figure 3:
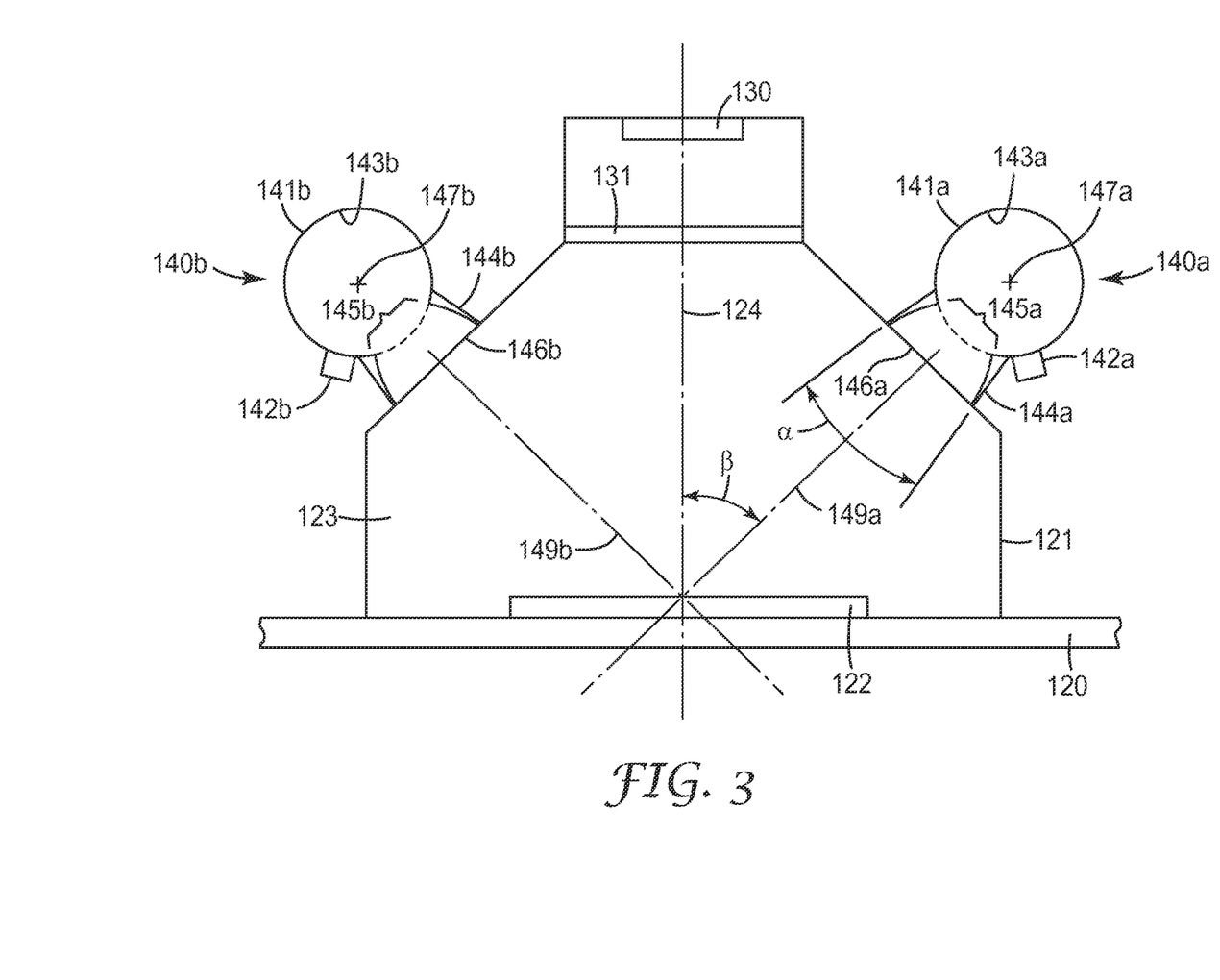
FIG. 3 is a side view illustrating the relative positions of the illumination modules and a camera used to obtain an image of the front surface of a growth plate on the plate support surface of FIG. 2.

FIG. 3 is a side view of the system depicted in FIG. 2 and is provided to depict additional details regarding the illumination modules 140a and 140b. The view of FIG. 3 includes plate support 120 with a growth plate 122 located thereon. The growth plate 122, in the depicted embodiment, is located within a volume 123 defined by housing 121, with an imaging device 130 positioned relative to an aperture 131 such that an image of the growth plate 122 on the plate support 120 can be obtained as described herein.

The illumination modules 140a and 140b may be positioned such that the light they emit is directed into the volume 123 of the housing 121 such that it illuminates a growth plate 122 located on the plate support 120. It may be preferred that the illumination modules 140a and 140b include transmissive panels 146a and 146b such that light can pass into the volume 123, but that debris cannot enter the illumination modules 140a and 140b.

The illumination modules 140a and 140b each include, in the depicted embodiment, a homogenization cavity 141a/141b, an extraction element 145a/145b, and a concentration element 144a/144b, along with one or more illumination sources 142a/142b.

In operation, light is emitted into the homogenization cavity 141a/141b by the one or more illumination sources 142a/142b. The interior surface 143a/143b of the homogenization cavity 141a/141b preferably homogenizes the light emitted by the illumination sources 142a/142b. As used herein, the "homogenization" may involve dispersing the light through diffuse reflection (e.g., Lambertian dispersion) from the interior surface 143a/143b and/or randomizing polarization of the light. The interior surface 143a/143b may be provided in a variety of different forms, although in some embodiments, the interior surface 143a/143b may be provided using a reflective interior coating such as, e.g., 6080 White Reflectance Coating from LABSPHERE, North Sutton, N.H. It may be preferred that the material used for the interior surfaces provide high reflectivity in combination with Lambertian dispersion. The homogenization cavity 141a/141b of the illumination module 140a/140b may be provided in the form of a cylinder that may preferably have a generally circular cross-sectional shape.

Light emitted into the homogenization cavity 141a/141b by the illumination source 142a/142b exits the cavity 141a/141b through an extraction element 145a/145b. The illumination source 142a/142b may be attached to the homogenization cavity 141a/141b such that light emitted by the illumination source 142a/142b must reflect from the interior surface 143a/143b at least once before exiting the homogenization cavity 141a/141b.

In some embodiments, the extraction element 145a/145b may be provided in the form of an opening in the homogenization cavity 141a/141b. It may be preferred that the extraction element 145a/145b be provided n the form of a elongated slot formed in the housing of the homogenization cavity 141a/141b. The extraction element 145a/145b may be open, i.e., in the form of void, in some embodiments. In other embodiments, the extraction element 145a/145b may be provided in the form of a transmissive window through which light can pass out of the homogenization cavity 141a/141b. Although only one extraction element 145a/145b is depicted in connection with each of the homogenization cavities 141a/141b, multiple extraction elements 145a/145b may be provided.

As depicted in FIG. 3, light exiting the homogenization cavity 141a/141b through the extraction element 145a/145b may be directed into a concentration element 144a/144b before it enters the volume 123 of the housing 121 in which the growth plate 122 is positioned on the plate support 120. The concentration element 144a/144b functions to control the angular range over which light is emitted by the illumination module 140a/140b. Control over the direction of the emitted light can potentially provide advantages such as, e.g., reducing reflections from the surface of the growth plate 122 that could potentially interfere with imaging of the growth plate, etc.

To achieve a selected degree of concentration/collimation of light, the concentration element 144a/144b may, in some embodiments, be provided as a pair of complementary parabolic surfaces. The interior reflective surfaces of the concentration element 144a/144b may, in some embodiments, be lined with reflective material that provides for diffuse reflection of light to reduce banding that might otherwise occur if the surfaces were specularly reflective. In other embodiments, the concentration element 144a/144b may be provided in the form of, e.g., another optical element that can provide for control over emission angles such as, e.g., a prismatic sheet (such as, e.g., VIKUITI Brightness Enhancement Film from 3M Company), etc. It may be preferred that the optical components used to illuminate the plate support 120 combine to provide light that has random polarization.

The concentration element 144a/144b and/or the illumination module 140a/140b may be described in terms of the angular range over which light is emitted. As seen in FIG. 3, the angular range α (alpha) is defined as the angular range containing 90 percent of the light emitted by an illumination module 140a/140b. The illumination module 140a/140b may also be defined as having an emission axis 149a/149b which can be described as a line (or plane) that is central to the angular range α (alpha) over which light is emitted from the illumination module 140a/140b.

The angular range α (alpha) may typically be determined by detecting rays incident on a surface oriented normal (perpendicular) to the emission axis 149a/149b of the illumination module 140a/140b. In connection with the apparatus described herein, some potentially useful values for the angular range α (alpha) as illustrated in FIG. 3 may be 60 degrees or less, 45 degrees or less, 30 degrees or less, 15 degrees or less, or even approaching zero (i.e., perfectly or nearly perfectly collimated light).

The illumination module 140a/140b may be arranged or oriented relative to the plate support 120 such that incidence angle β (beta) formed between the emission axis 149a/149b of the illumination module 140a/140b and a normal axis 124 is within an acceptable range (which is preferably a range that can potentially enhance imaging of the growth plate 122 by the imaging device 130). The normal axis 124 is generally perpendicular to the imaging plane defined by the upper surface of the growth plate 122 on plate support 120 in FIG. 3. At the upper end of the range, the incidence angle β (beta) may be within a range of 75 degrees or less, 70 degrees or less, or even 65 degrees or less. At the lower end of the range, the incidence angle β (beta) may be within a range of 50 degrees or more, 55 degrees or more, 60 degrees or more, or even 65 degrees or more.

In some embodiments, the illumination modules 140a/140b may emit light that is directly incident on substantially the entire surface of a growth plate 122 located on the plate support 120. In some embodiments, the illumination modules 140a/140b may emit light that is directly incident on substantially the entire surface of the plate support 120 (which may, in some embodiments, be of a different size than the growth plate 122).

The variables discussed above, i.e., angular range α (alpha) and the incidence angle β (beta), are preferably selected to provide the desired illumination of the plate support 120 (and/or a growth plate 122 located thereon). Yet another variable that may impact the area of illumination is the distance between the illumination module 140a/140b and the plate support 120 (and/or growth plate 122). As that distance increases, the illuminated area will also increase assuming that the angular range α (alpha) and the incidence angle β (beta) remain constant. If, conversely, that distance remains constant, changes in the angular range α (alpha) and/or the incidence angle β (beta) can affect the size of the area illuminated by the illumination modules 140a/140b.

In one embodiment, for example, the illumination modules 140a/140b each provide light over a selected angular range α (alpha) of about 45 degrees. The illumination modules are further oriented relative to the plate surface 120 with an incidence angle β (beta) of about 70 degrees. The illumination modules 140a/140b are located at a distance from the plate support such that each illumination module 140a and 140b emits light that is directly incident on an area of the plate support 120 having a width of about 80 millimeters (mm) which, in the depicted embodiment is approximately equivalent to the width of the growth plate 122.

In embodiments that include two or more illumination modules used to illuminate that same plate support surface, the characteristics of the two or more illumination modules (e.g., angular range angular range α (alpha), incidence angle β (beta), etc.) may be the same or they may be different.

The net result of control over the illumination provided to a growth plate by the illumination modules used in the biological growth plate scanners described herein may be that flat field uniformity is obtained over the surface to be imaged. In some embodiments, illumination modules used in a system may illuminate the plate support surface 120 with an illumination intensity that varies by ±10% or less over the plate support surface. In other embodiments, the illumination modules described herein may be capable of achieving illumination intensity that varies by ±5% or less over the plate support surface.

The uniformity of the illumination intensity on the plate support surface 120 may, in some embodiments, be adjusted by changing the incidence angle β (beta) of each of the illumination modules 140a/140b. The incidence angle β (beta) may be adjusted in at least some embodiments by rotating the illumination modules 140a/140b about their respective longitudinal axes 147a/147b (which are depicted in FIGS. 2 and 3), with the rotation changing the angle at which the light is incident on the plate support surface. In other embodiments, the illumination modules 140a/140b may be rotated about other axes that are generally aligned with the longitudinal axes 147a/147b of the homogenization cavities to adjust the incidence angle β (beta) of an illumination module. Adjustment of one or both of the incidence angles β (beta) may be used to improve the uniformity of the illumination provided to the plate support surface.

Although not depicted in FIG. 3, the biological growth plate scanners described herein may include a back illumination apparatus (see item 50 in FIG. 1). In such systems, the plate support 120 may be transmissive such that light from a back illumination apparatus can be transmitted through the plate support such that it reaches the back surface of the growth plate 122 (wherein the back surface of the growth plate 122 is the surface facing the plate support 120).

EMBODIMENTS

Embodiment 1 is an illumination apparatus for illuminating biological growth plates in a biological growth plate scanner, the apparatus comprising:
 a plate support surface comprising a first side and a second side located opposite from the first side; and
 a first illumination module oriented to illuminate a first portion of the plate support surface, wherein the first illumination module comprises:
  a homogenization cavity comprising an interior surface, wherein the interior surface is diffusely reflective, wherein the interior surface of the homogenization cavity comprises a tube that comprises a longitudinal axis extending along a length of the homogenization cavity, and wherein the longitudinal axis is aligned with the first side of the plate support surface;
  an illumination source operably connected to the homogenization cavity, wherein the illumination source emits light into the homogenization cavity;
  an extraction element in the homogenization cavity through which the light emitted into the homogenization cavity exits from the homogenization cavity, wherein the extraction element comprises a length aligned with the longitudinal axis, and wherein the illumination source, the interior surface of the homogenization cavity, and the extraction element are arranged such that the light emitted into the homogenization cavity by the illumination source reflects from the interior surface of the homogenization cavity at least once before exiting the homogenization cavity through the extraction element;

a concentration element operably connected to the homogenization cavity and arranged such that the light exiting the homogenization cavity through the extraction element must pass through the concentration element; wherein the light passing through the concentration element from the extraction element exits from the concentration element within a selected angular range α (alpha) of 60 degrees or less.

Embodiment 2 is an apparatus according to embodiment 1, wherein the first portion of the plate support surface comprises substantially all of the plate support surface.

Embodiment 3 is an apparatus according to embodiment 1, wherein the plate support surface defines an imaging plane, and wherein the concentration element comprises a central emission axis within a center of the angular range α (alpha), and further wherein the central emission axis forms an incidence angle β (beta) with an axis normal to the imaging plane that is 75 degrees or less.

Embodiment 4 is an apparatus according to embodiment 3, wherein the incidence angle β (beta) is 50 degrees or more.

Embodiment 5 is an apparatus according to embodiment 4, wherein the selected angular range α (alpha) of the concentration element is 45 degrees or less.

Embodiment 6 is an apparatus according to embodiment 5, wherein the incidence angle β (beta) and the selected angular range α (alpha) are selected such that the plate support surface is illuminated with an illumination intensity that varies by ±10% or less over the plate support surface.

Embodiment 7 is an apparatus according to embodiment 1, wherein the tube of the homogenization cavity comprises a circular cylindrical tube.

Embodiment 8 is an apparatus according to embodiment 1, wherein the plate support surface defines an imaging plane, and wherein the concentration element comprises a central emission axis within a center of the angular range α (alpha), wherein the central emission axis forms an incidence angle β (beta) with an axis normal to the imaging plane, and further wherein the first illumination module rotates relative to the longitudinal axis of the homogenization cavity to adjust the incidence angle β (beta).

Embodiment 9 is an apparatus according to embodiment 8, wherein the first illumination module rotates about the longitudinal axis of the homogenization cavity.

Embodiment 10 is an apparatus according to embodiment 1, wherein the concentration element comprises a pair of parabolic surfaces.

Embodiment 11 is an apparatus according to embodiment 10, wherein the parabolic surfaces comprise diffusely reflective surfaces.

Embodiment 12 is an apparatus according to any one of embodiments 1-11, the apparatus further comprising a second illumination module oriented to illuminate a second portion of the plate support surface, wherein the second illumination module comprises:

a homogenization cavity comprising an interior surface, wherein the interior surface is diffusely reflective, wherein the interior surface of the homogenization cavity comprises a tube that comprises a longitudinal axis extending along a length of the homogenization cavity, and wherein the longitudinal axis is aligned with the second side of the plate support surface;

an illumination source operably connected to the homogenization cavity, wherein the illumination source emits light into the homogenization cavity;

an extraction element in the homogenization cavity through which the light emitted into the homogenization cavity exits from the homogenization cavity, wherein the extraction element comprises a length aligned with the longitudinal axis, and wherein the illumination source, the interior surface of the homogenization cavity, and the extraction element are arranged such that the light emitted into the homogenization cavity by the illumination source reflects from the interior surface of the homogenization cavity at least once before exiting the homogenization cavity through the extraction element;

a concentration element operably connected to the homogenization cavity and arranged such that the light exiting the homogenization cavity through the extraction element must pass through the concentration element; wherein the light passing through the concentration element from the extraction element exits from the concentration element within a selected angular range α (alpha) of 60 degrees or less.

Embodiment 13 is an apparatus according to embodiment 12, wherein the second portion of the plate support surface comprises substantially all of the plate support surface.

Embodiment 14 is an apparatus according to embodiment 12, wherein the plate support surface defines an imaging plane, and wherein the concentration element of the second illumination module comprises a central emission axis within a center of the angular range α (alpha), and further wherein the central emission axis forms an incidence angle β (beta) with an axis normal to the imaging plane that is 75 degrees or less.

Embodiment 15 is an apparatus according to embodiment 14, wherein the incidence angle β (beta) of the second illumination module is 50 degrees or more.

Embodiment 16 is an apparatus according to embodiment 15, wherein the selected angular range α (alpha) of the concentration element of the second illumination module is 45 degrees or less.

Embodiment 17 is an apparatus according to embodiment 16, wherein the incidence angle β (beta) and the selected angular range α (alpha) for each of the first illumination module and the second illumination module are selected such that the plate support surface is illuminated with an illumination intensity that varies by ±10% or less over the plate support surface.

Embodiment 18 is an apparatus according to embodiment 12, wherein the tube of the homogenization cavity of the second illumination module comprises a circular cylindrical tube.

Embodiment 19 is an apparatus according to embodiment 12, wherein the plate support surface defines an imaging plane, and wherein the concentration element of the second illumination module comprises a central emission axis within a center of the angular range α (alpha), wherein the central emission axis forms an incidence angle β (beta) with an axis normal to the imaging plane, and further wherein the second illumination module rotates relative to the longitudinal axis of the homogenization cavity of the second illumination module to adjust the incidence angle β (beta).

Embodiment 20 is an apparatus according to embodiment 19, wherein the second illumination module rotates about the longitudinal axis of the homogenization cavity of the second illumination module.

Embodiment 21 is an apparatus according to embodiment 12, wherein the concentration element of the second illumination module comprises a pair of parabolic surfaces.

Embodiment 22 is an apparatus according to embodiment 21, wherein the parabolic surfaces of the concentration element of the second illumination module comprise diffusely reflective surfaces.

Embodiment 23 is a method of illuminating a plate support surface of biological growth plate scanner, the method comprising:
 positioning a growth plate on the plate support surface of an apparatus according to embodiment 12; and
 illuminating the growth plate using the first and second illumination modules.

Embodiment 24 is a method according to embodiment 23, the method further comprising:
 rotating the first illumination module relative to the longitudinal axis of the homogenization cavity of the first illumination module;
 measuring the illumination intensity across the plate support surface after and/or while rotating the first illumination module.

Embodiment 25 is a method according to embodiment 24, wherein the rotating comprises rotating the first illumination module about the longitudinal axis of the homogenization cavity of the first illumination module.

Embodiment 26 is a biological growth plate scanner comprising:
 an imaging device;
 an image processor operably connected to the imaging device; and
 an illumination apparatus according to any one of embodiments 1-22.

The complete disclosure of the patents, patent documents, and publications cited herein are incorporated by reference in their entirety as if each were individually incorporated (to the extent they do not conflict with the disclosure contained in this document).

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. An illumination apparatus for illuminating biological growth plates in a biological growth plate scanner, the apparatus comprising:
 a plate support surface comprising a first side and a second side located opposite from the first side;
 a first illumination module oriented to illuminate a first portion of the plate support surface, wherein the first illumination module comprises:
  a homogenization cavity comprising an interior surface, wherein the interior surface is diffusely reflective, wherein the interior surface of the homogenization cavity comprises a tube that comprises a longitudinal axis extending along a length of the homogenization cavity, and wherein the longitudinal axis is aligned with the first side of the plate support surface;
  an illumination source operably connected to the homogenization cavity, wherein the illumination source emits light into the homogenization cavity;
  an extraction element in the homogenization cavity through which the light emitted into the homogenization cavity exits from the homogenization cavity, wherein the extraction element comprises a length aligned with the longitudinal axis, and wherein the illumination source, the interior surface of the homogenization cavity, and the extraction element are arranged such that the light emitted into the homogenization cavity by the illumination source reflects from the interior surface of the homogenization cavity at least once before exiting the homogenization cavity through the extraction element;
  a concentration element disposed outside the homogenization cavity and operably connected to the homogenization cavity and arranged such that the light exiting the homogenization cavity through the extraction element must pass through the concentration element; wherein the light passing through the concentration element from the extraction element exits from the concentration element within a selected angular range α (alpha) of 60 degrees or less;
 wherein the light exiting the homogenization cavity comprises a central emission axis within a center of the angular range α (alpha), wherein a line extending from the homogenization cavity along the central emission axis is directly incident on the plate support surface.

2. An apparatus according to claim 1, wherein the first portion of the plate support surface comprises substantially all of the plate support surface.

3. An apparatus according to claim 1, wherein the plate support surface defines an imaging plane, wherein the central emission axis forms an incidence angle β (beta) with an axis normal to the imaging plane that is 75 degrees or less.

4. An apparatus according to claim 3, wherein the incidence angle β (beta) is 50 degrees or more.

5. An apparatus according to claim 4, wherein the selected angular range a (alpha) of the concentration element is 45 degrees or less.

6. An apparatus according to claim 5, wherein the incidence angle β (beta) and the selected angular range α (alpha) are selected such that the plate support surface is illuminated with an illumination intensity that varies by ±10% or less over the plate support surface.

7. An apparatus according to claim 1, wherein the tube of the homogenization cavity comprises a circular cylindrical tube.

8. An apparatus according to claim 1, wherein the plate support surface defines an imaging plane, and wherein the concentration element comprises a central emission axis within a center of the angular range α (alpha), wherein the central emission axis forms an incidence angle β (beta) with an axis normal to the imaging plane, and further wherein the first illumination module rotates relative to the longitudinal axis of the homogenization cavity to adjust the incidence angle β (beta).

9. An apparatus according to claim 8, wherein the first illumination module rotates about the longitudinal axis of the homogenization cavity.

10. An apparatus according to claim 1, wherein the concentration element comprises a pair of parabolic surfaces.

11. An apparatus according to claim 10, wherein the parabolic surfaces comprise diffusely reflective surfaces.

12. An apparatus according to claim 1, the apparatus further comprising a second illumination module oriented to illuminate a second portion of the plate support surface, wherein the second illumination module comprises:

a homogenization cavity comprising an interior surface, wherein the interior surface is diffusely reflective, wherein the interior surface of the homogenization cavity comprises a tube that comprises a longitudinal axis extending along a length of the homogenization cavity, and wherein the longitudinal axis is aligned with the second side of the plate support surface;

an illumination source operably connected to the homogenization cavity, wherein the illumination source emits light into the homogenization cavity;

an extraction element in the homogenization cavity through which the light emitted into the homogenization cavity exits from the homogenization cavity, wherein the extraction element comprises a length aligned with the longitudinal axis, and wherein the illumination source, the interior surface of the homogenization cavity, and the extraction element are arranged such that the light emitted into the homogenization cavity by the illumination source reflects from the interior surface of the homogenization cavity at least once before exiting the homogenization cavity through the extraction element;

a concentration element disposed outside the homogenization cavity and operably connected to the homogenization cavity and arranged such that the light exiting the homogenization cavity through the extraction element must pass through the concentration element; wherein the light passing through the concentration element from the extraction element exits from the concentration element within a selected angular range α (alpha) of 60 degrees or less;

wherein the light exiting the homogenization cavity comprises a central emission axis within a center of the angular range α (alpha), wherein a line extending from the homogenization cavity along the central emission axis is directly incident on the plate support surface.

13. An apparatus according to claim 12, wherein the second portion of the plate support surface comprises substantially all of the plate support surface.

14. An apparatus according to claim 12, wherein the plate support surface defines an imaging plane, and wherein the concentration element of the second illumination module comprises a central emission axis within a center of the angular range α (alpha), and further wherein the central emission axis forms an incidence angle β (beta) with an axis normal to the imaging plane that is 75 degrees or less.

15. An apparatus according to claim 14, wherein the incidence angle β (beta) of the second illumination module is 50 degrees or more.

16. An apparatus according to claim 15, wherein the selected angular range α (alpha) of the concentration element of the second illumination module is 45 degrees or less.

17. An apparatus according to claim 16, wherein the incidence angle β (beta) and the selected angular range α (alpha) for each of the first illumination module and the second illumination module are selected such that the plate support surface is illuminated with an illumination intensity that varies by ±10% or less over the plate support surface.

18. An apparatus according to claim 12, wherein the tube of the homogenization cavity of the second illumination module comprises a circular cylindrical tube.

19. An apparatus according to claim 12, wherein the plate support surface defines an imaging plane, and wherein the concentration element of the second illumination module comprises a central emission axis within a center of the angular range α (alpha), wherein the central emission axis forms an incidence angle β (beta) with an axis normal to the imaging plane, and further wherein the second illumination module rotates relative to the longitudinal axis of the homogenization cavity of the second illumination module to adjust the incidence angle β (beta).

20. An apparatus according to claim 19, wherein the second illumination module rotates about the longitudinal axis of the homogenization cavity of the second illumination module.

21. An apparatus according to claim 12, wherein the concentration element of the second illumination module comprises a pair of parabolic surfaces.

22. An apparatus according to claim 21, wherein the parabolic surfaces of the concentration element of the second illumination module comprise diffusely reflective surfaces.

23. A method of illuminating a plate support surface of biological growth plate scanner, the method comprising:
    providing the apparatus of claim 12;
    positioning a growth plate on the plate support surface; and
    illuminating the growth plate using the first and second illumination modules.

24. A method according to claim 23, the method further comprising:
    rotating the first illumination module relative to the longitudinal axis of the homogenization cavity of the first illumination module;
    measuring the illumination intensity across the plate support surface after and/or while rotating the first illumination module;
    wherein the first illumination module is rotatable with respect to the longitudinal axis of the homogenization cavity of the first illumination module.

25. A biological growth plate scanner comprising:
    an imaging device;
    an image processor operably connected to the imaging device; and
    an illumination apparatus according to claim 1.

* * * * *

UNITED STATES PATENT AND TRADEMARK OFFICE
CERTIFICATE OF CORRECTION

PATENT NO. : 8,840,840 B2  Page 1 of 1
APPLICATION NO. : 13/513900
DATED : September 23, 2014
INVENTOR(S) : Phillip A. Bolea It is certified that error appears in the above-identified patent and that said Letters Patent is hereby corrected as shown below:

In the Specification:

Column 3,
Line 38, "modules.'" should read --modules.--.

Column 8,
Line 32, "n" should read --in--.
Line 32, "a" should read --an--.

In the Claims:

Column 14,
Line 38, "range a" should read --range α--.

Signed and Sealed this
First Day of December, 2015

Michelle K. Lee
*Director of the United States Patent and Trademark Office*